United States Patent
Frey et al.

(10) Patent No.: US 9,193,921 B2
(45) Date of Patent: Nov. 24, 2015

(54) HYDROCRACKING PROCESS FOR A HYDROCARBON STREAM

(71) Applicant: UOP LLC, Des Plaines, IL (US)

(72) Inventors: Stanley J. Frey, Palatine, IL (US); Paul T. Barger, Arlington Heights, IL (US); Maureen L. Bricker, Buffalo Grove, IL (US); John Q. Chen, Glenview, IL (US); Peter K. Coughlin, Mundelein, IL (US); James A. Johnson, Burr Rigde, IL (US); Joseph A. Kocal, Glenview, IL (US); Matthew Lippmann, Chicago, IL (US); Vasant P. Thakkar, Elk Grove Village, IL (US); Kurt M. Vanden Bussche, Lake in the Hills, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/718,573

(22) Filed: May 21, 2015

(65) Prior Publication Data

US 2015/0259612 A1 Sep. 17, 2015

Related U.S. Application Data

(62) Division of application No. 14/472,096, filed on Aug. 28, 2014, now Pat. No. 9,073,805.

(60) Provisional application No. 61/905,964, filed on Nov. 19, 2013.

(51) Int. Cl.
| | |
|---|---|
| C07C 4/04 | (2006.01) |
| C07C 4/06 | (2006.01) |
| C07C 4/12 | (2006.01) |
| C10G 47/00 | (2006.01) |
| C10G 45/00 | (2006.01) |
| C10G 65/12 | (2006.01) |
| C10G 1/00 | (2006.01) |

(52) U.S. Cl.
CPC . *C10G 65/12* (2013.01); *C07C 4/04* (2013.01); *C10G 1/002* (2013.01)

(58) Field of Classification Search
USPC .......... 585/652, 320; 208/107, 208 R, 251 R, 208/254 R, 400
See application file for complete search history.

(56) References Cited

U.S. PATENT DOCUMENTS

2013/0267744 A1* 10/2013 Kim et al. ................ 585/251

* cited by examiner

*Primary Examiner* — Thuan D Dang

(57) ABSTRACT

A process for transalkylating a coal tar stream is described. A coal tar stream is provided, and is fractionated to provide at least one hydrocarbon stream having polycyclic aromatics. The hydrocarbon stream is hydrotreated in a hydrotreating zone, and then hydrocracked in a hydrocracking zone. A light aromatics stream is added to the hydrocracking zone. The light aromatics stream comprises one or more light aromatics having a ratio of methyl/aromatic available position that is lower than a ratio of methyl/aromatic available position for the hydrotreated stream. The hydrocracked stream is transalkylated in the hydrocracking zone.

6 Claims, 3 Drawing Sheets

HYDROCRACKING PROCESS FOR A HYDROCARBON STREAM

CROSS-REFERENCE TO RELATED APPLICATIONS

This application is a Division of application Ser. No. 14/472,096 filed Aug. 28, 2014, now U.S. Pat. No. 9,073,805 which application claims priority from Provisional Application No. 61/905,964 filed Nov. 19, 2013, the contents of which are hereby incorporated by reference.

BACKGROUND OF THE INVENTION

Many different types of chemicals are produced from the processing of petroleum. However, petroleum is becoming more expensive because of increased demand in recent decades.

Therefore, attempts have been made to provide alternative sources for the starting materials for manufacturing chemicals. Attention is now being focused on producing liquid hydrocarbons from solid carbonaceous materials, such as coal, which is available in large quantities in countries such as the United States and China.

Pyrolysis of coal produces coke and coal tar. The coke-making or "coking" process consists of heating the material in closed vessels in the absence of oxygen to very high temperatures. Coke is a porous but hard residue that is mostly carbon and inorganic ash, which is used in making steel.

Coal tar is the volatile material that is driven off during heating, and it comprises a mixture of a number of hydrocarbon compounds. It can be separated to yield a variety of organic compounds, such as benzene, toluene, xylene, naphthalene, anthracene, and phenanthrene. These organic compounds can be used to make numerous products, for example, dyes, drugs, explosives, flavorings, perfumes, preservatives, synthetic resins, and paints and stains. The residual pitch left from the separation is used for paving, roofing, waterproofing, and insulation.

There is a need for additional processes for increasing the yield of desirable aromatics, such as xylenes, from hydrocarbons such as coal tar organic compounds.

SUMMARY OF THE INVENTION

One aspect of the invention involves a process for transalkylating a coal tar stream. A coal tar stream is provided, and is fractionated to provide at least one hydrocarbon stream having polycyclic aromatics. The hydrocarbon stream is hydrotreated in a hydrotreating zone, and then hydrocracked in a hydrocracking zone. A light aromatics stream is added to the hydrocracking zone. The light aromatics stream comprises one or more light aromatics having a ratio of methyl/aromatic available position that is lower than a ratio of methyl/aromatic available position for the hydrotreated stream. An aromatic available position is defined as a carbon in an aromatic ring that has not had the hydrogen atom bonded to it substituted with a carbon that is also part of another cyclic ring—aromatic or naphthenic. The hydrocracked stream is transalkylated in the hydrocracking zone.

Another aspect of the invention provides a process for hydrogenating a coal tar stream. The coal tar stream is fractionated to provide at least one hydrocarbon stream comprising polycyclic aromatics. The hydrocarbon stream is introduced to a hydrocracking zone. The hydrocarbon stream is hydrocracked in the hydrocracking zone to convert a first portion of the polycyclic aromatics to monocyclic aromatics. A second portion of the polycyclic aromatics is hydrogenated to form a hydrogen donor molecule.

Another aspect of the invention provides a process for hydrogenating a hydrocarbon stream. The hydrocarbon stream is fractionated to provide at least one hydrocarbon stream comprising polycyclic aromatics. The fractionated stream is introduced to a hydrocracking zone. The fractionated stream is hydrocracked in the hydrocracking zone to convert a first portion of the polycyclic aromatics to monocyclic aromatics. A second portion of the polycyclic aromatics is hydrogenated to form a hydrogen donor molecule.

DETAILED DESCRIPTION OF THE INVENTION

Figure 1:
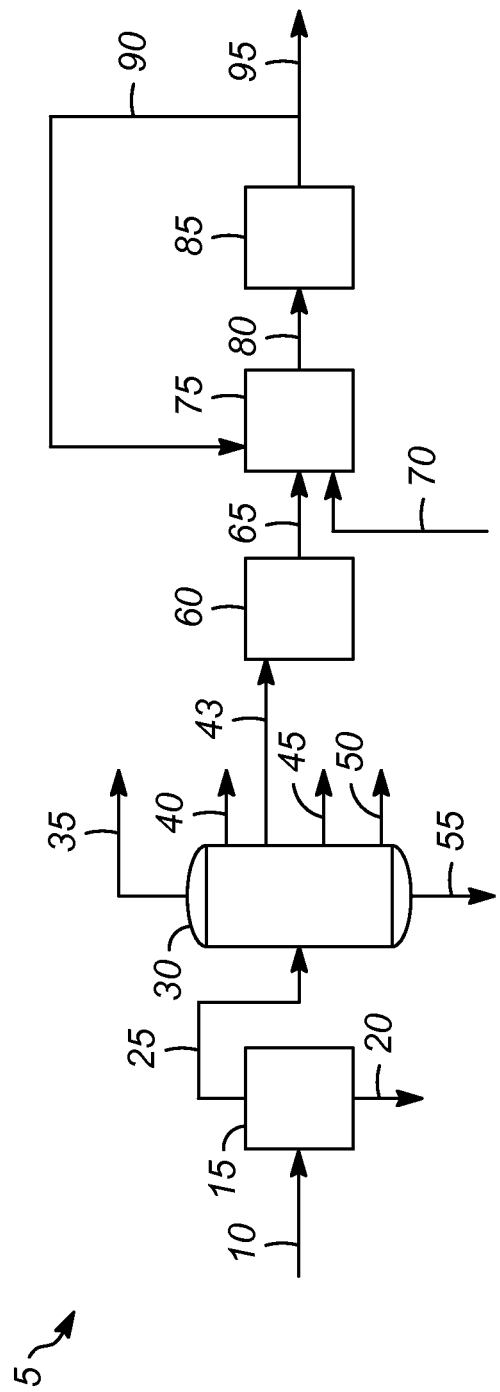
FIG. 1 is an illustration of a first embodiment process of the present invention.

FIG. 1 shows one embodiment of a basic coal conversion process 5. A coal tar stream is provided, such as by a coal feed 10 that is fed to a pyrolysis zone 15, e.g., a coking oven. In the pyrolysis zone 15, the coal is heated at high temperature, e.g., up to about 2,000° C. (3600° F.), in the absence of oxygen to drive off the volatile components. Coking produces a coke stream 20 and a coal tar stream 25. The coke stream 20 can be used in other processes, such as the manufacture of steel. In other embodiments, the coal tar stream 25 is obtained from other sources.

In some processes, all or a portion of the coal feed 10 is mixed with oxygen and steam and reacted under heat and pressure in a gasification zone (not shown) to form syngas, which is a mixture of carbon monoxide and hydrogen. The syngas can be further processed using the Fischer-Tropsch reaction to produce gasoline or using the water-gas shift reaction to produce more hydrogen.

The coal tar stream 25 is fractionated in a fractionation zone 30. Coal tar comprises a complex mixture of heterocyclic aromatic compounds and their derivatives with a wide range of boiling points. The number of fractions and the components in the various fractions can be varied as is well known in the art. A typical separation process involves separating the coal tar stream 25 into four to six streams. For example, there can be a fraction 35 comprising $NH_3$, CO, and light hydrocarbons, a light oil fraction 40 with boiling points between 0° C. and 180° C., a middle oil fraction 43 with boiling points between 180° C. to 230° C., a heavy oil fraction 45 with boiling points between 230 to 270° C., an anthracene oil fraction 50 with boiling points between 270° C. to 350° C., and pitch 55.

The light oil fraction 40 contains compounds such as benzenes, toluenes, xylenes, naphtha, coumarone-indene, dicyclopentadiene, pyridine, and picolines. The middle oil fraction 43 contains compounds such as phenols, cresols and cresylic acids, xylenols, naphthalene, high boiling tar acids, and high boiling tar bases. The heavy oil fraction 45 contains benzene absorbing oil and creosotes. The anthracene oil fraction 50 contains anthracene. Pitch 55 is the residue of the coal tar distillation containing primarily aromatic hydrocarbons and heterocyclic compounds.

At least one hydrocarbon stream, such as the light oil fraction 40, the middle oil fraction 43 (as shown in FIG. 1), or the heavy oil fraction 45 is preferably hydrotreated in a hydrotreating zone 60. Hydrotreating is a process in which hydrogen gas is contacted with a hydrocarbon stream in the presence of suitable catalysts which are primarily active for the removal of heteroatoms, such as sulfur, nitrogen, and metals from the hydrocarbon feedstock. In hydrotreating, hydrocarbons with double and triple bonds may be saturated. Aromatics may also be saturated. Typical hydrotreating reaction conditions include a temperature of about 290° C. (550° F.) to about 455° C. (850° F.), a pressure of about 3.4 MPa (500 psig) to about 26.7 MPa (4000 psig), a liquid hourly space velocity of about 0.5 hr$^{-1}$ to about 4 hr$^{-1}$, and a hydrogen rate of about 168 to about 1,011 Nm$^3$/m$^3$ oil (1,000-6,000 scf/bbl). Typical hydrotreating catalysts include at least one Group VIII metal, preferably iron, cobalt and nickel, and at least one Group VI metal, preferably molybdenum and tungsten, on a high surface area support material, preferably alumina. Other typical hydrotreating catalysts include zeolitic catalysts, as well as noble metal catalysts where the noble metal is selected from palladium and platinum.

A hydrotreated stream 65 from the hydrotreating zone 60 is delivered to a hydrocracking zone 75. Hydrocracking is a process in which hydrocarbons crack in the presence of hydrogen to lower molecular weight hydrocarbons. Typical hydrocracking conditions may include a temperature of about 290° C. (550° F.) to about 468° C. (875° F.), and a liquid hourly space velocity (LHSV) of about 1.0 to less than about 2.5 hr$^{-1}$, and a hydrogen rate of about 421 to about 2,527 Nm$^3$/m$^3$ oil (2,500-15,000 scf/bbl). Typical hydrocracking catalysts include amorphous silica-alumina bases or low-level zeolite bases combined with one or more Group VIII or Group VIB metal hydrogenating components, or a crystalline zeolite cracking base upon which is deposited a Group VIII metal hydrogenating component. Additional hydrogenating components may be selected from Group VIB for incorporation with the zeolite base. Hydrotreating and hydrocracking crack polycyclic aromatics in the hydrocarbon stream to mono-aromatics, and saturate mono-aromatics to cycloparaffins. A light aromatic stream 70 is added to the hydrocracking zone 75 for transalkylating the hydrocracked stream in the hydrocracking zone. The light aromatics stream 70 includes one or more light aromatics having a ratio of methyl/aromatic available position that is lower than a ratio of methyl/aromatic available position for the hydrotreated stream 65. Suitable light aromatics include, but are not limited to benzene, toluene, ethylbenzene, propylbenzene, indane, and butylbenzene.

Transalkylation is a chemical reaction resulting in transfer of an alkyl group from one organic compound to another. Catalysts, particularly zeolite catalysts, can be used to effect the reaction. The transalkylation transalkylates primarily methyl alkyl groups. This is useful, for example, to produce dimethylbenzenes, a desirable chemical family of xylenes. These catalysts systems promote the transfer of methyl groups, long chain alkyl groups such as ethyl, propyl and butyl groups are largely dealkylated. If desired, the transalkylation catalyst may be metal stabilized using a noble metal or base metal, and may contain suitable binder or matrix material such as inorganic oxides and other suitable materials. In a transalkylation process, a polyalkylaromatic hydrocarbon feed and an aromatic hydrocarbon feed are provided to a transalkylation reaction zone. The feed is usually heated to reaction temperature and then passed through a reaction zone, which may comprise one or more individual reactors. Passage of the combined feed through the reaction zone produces an effluent stream closer to the equilibrium of the distribution of methyl groups than the incoming feed stream. This effluent is normally cooled and passed to a stripping column in which substantially all C5 and lighter hydrocarbons present in the effluent are concentrated into an overhead stream and removed from the process. An aromatics-rich stream is recovered as net stripper bottoms, which is referred to as the transalkylation effluent.

The transalkylation reaction can be effected in contact with a catalytic composite in any conventional or otherwise convenient manner and may comprise a batch or continuous type of operation, with a continuous operation being preferred. The transalkylation catalyst is usefully disposed as a fixed bed in a reaction zone of a vertical tubular reactor, with the alkylaromatic feed stock charged through the bed in an upflow or downflow manner. Fluidized beds as described below could also be used. The transalkylation zone normally operates at conditions including a temperature in the range of about 130° C. to about 540° C. The transalkylation zone is typically operated at moderately elevated pressures broadly ranging from about 100 kPa to about 10 MPa absolute. The transalkylation reaction can be effected over a wide range of space velocities. That is, volume of charge per volume of catalyst per hour; weight hourly space velocity (WHSV) generally is in the range of from about 0.1 to about 30 hr$^{-1}$. The catalyst is typically selected to have relatively high stability at a high activity level.

An example pressure range for the hydrocracking and transalkylation within the hydrocracking zone 75 is between about 1.4 MPa (200 psig) to about 17.24 (2500 psig). The transalkylation of polycyclic aromatics within the hydrocracking zone 75 transalkylates methyl groups to the light aromatics, and provides a greater portion of xylenes in the effluent stream 80.

The effluent stream 80 from the hydrocracking zone 75 can be fed to a dehydrogenation zone 85, where cycloparaffins in the effluent stream are converted to aromatics. Example dehydrogenation conditions include a pressure between about 0.2 MPa (30 psig) to about 3.5 MPa (500 psig) and about 427° C. (800° F.) to about 538° C. (1000° F.). Example catalysts include naphtha reforming catalyst and paraffin dehydrogenation catalysts. Particular example catalysts include platinum and bi-metallic Pt—Re, Pt—Sn on alumina and chloride alumina.

The effluent stream 95 from the dehydrogenation zone 85 can include one or more of A9+ aromatics, benzene, and toluene. At least a portion 90 of the A9+ aromatics, benzene, and toluene can be recycled from the dehydrogenation zone 85 to the hydrocracking zone 75, if desired. At least a portion of the effluent stream 95 can alternatively or additionally be subjected to downstream conversion or other processing to provide one or more products. Examples include hydrotreating zones, hydrocracking zones, fluid catalytic cracking zones, alkylation zones, transalkylation zones, oxidation zones, and hydrogenation zones.

Example hydrotreating and hydrocracking processes are discussed above. Conditions for additional hydrotreating include a temperature of about 290° C. (550° F.) to about 455° C. (850° F.), a pressure of about 3.4 MPa (500 psig) to about 27.6 MPa (4000 psig), a liquid hourly space velocity of about 0.5 hr$^{-1}$ to about 4 hr$^{-1}$, and a hydrogen rate of about 168 to about 1,011 Nm3/m3 oil (1,000-6,000 scf/bbl). Example conditions for additional hydrocracking include a temperature of about 290° C. (550° F.) to about 468° C. (875° F.), a pressure of about 3.5 MPa (500 psig) to about 20.7 MPa (3000 psig), a liquid hourly space velocity (LHSV) of about 1.0 to less than about 2.5 hr$^{-1}$, and a hydrogen rate of about 421 to about 2,527 Nm$^3$/m$^3$ oil (2,500-15,000 scf/bbl).

Fluid catalytic cracking (FCC) is a catalytic hydrocarbon conversion process accomplished by contacting heavier hydrocarbons in a fluidized reaction zone with a catalytic particulate material. The reaction in catalytic cracking is carried out in the absence of substantial added hydrogen or the consumption of hydrogen. The process typically employs a spray-dried catalyst having the particles suspended in a rising flow of feed hydrocarbons to form a fluidized bed. In representative processes, cracking takes place in a riser, which is a vertical or upward sloped pipe. Typically, a pre-heated feed is sprayed into the base of the riser via feed nozzles where it contacts hot fluidized catalyst and is vaporized on contact with the catalyst, and the cracking occurs converting the high molecular weight oil into lighter components including liquefied petroleum gas (LPG), gasoline, and a distillate. The catalyst-feed mixture flows upward through the riser for a short period (a few seconds), and then the mixture is separated in cyclones. The hydrocarbons are directed to a fractionator for separation into LPG, gasoline, diesel, kerosene, jet fuel, and other possible fractions. While going through the riser, the cracking catalyst is deactivated because the process is accompanied by formation of coke which deposits on the catalyst particles. Contaminated catalyst is separated from the cracked hydrocarbon vapors and is further treated with steam to remove hydrocarbon remaining in the pores of the catalyst. The catalyst is then directed into a regenerator where the coke is burned off the surface of the catalyst particles, thus restoring the catalyst's activity and providing the necessary heat for the next reaction cycle. The process of cracking is endothermic. The regenerated catalyst is then used in the new cycle. Typical FCC conditions include a temperature of about 400° C. to about 800° C., a pressure of about 0 to about 688 kPa g (about 0 to 100 psig), and contact times of about 0.1 seconds to about 1 hour. The conditions are determined based on the hydrocarbon feedstock being cracked, and the cracked products desired. Zeolite-based catalysts are commonly used in FCC reactors, as are composite catalysts which contain zeolites, silica-aluminas, alumina, and other binders.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. toluene, xylenes, ethylbenzene, etc.). For isobutene alkylation, typically, the reactants are mixed in the presence of a strong acid catalyst, such as sulfuric acid or hydrofluoric acid. The alkylation reaction is carried out at mild temperatures, and is typically a two-phase reaction. Because the reaction is exothermic, cooling is needed. Depending on the catalyst used, normal refinery cooling water provides sufficient cooling. Alternatively, a chilled cooling medium can be provided to cool the reaction. The catalyst protonates the alkenes to produce reactive carbocations which alkylate the isobutane reactant, thus forming branched chain paraffins from isobutane. Aromatic alkylation is generally now conducted with solid acid catalysts including zeolites or amorphous silica-aluminas The alkylation reaction zone is maintained at a pressure sufficient to maintain the reactants in liquid phase. For a hydrofluoric acid catalyst, a general range of operating pressures is from about 200 to about 7100 kPa absolute. The temperature range covered by this set of conditions is from about −20° C. to about 200° C. For at least alkylation of aromatic compounds, the temperature range is about from 100-200° C. at the pressure range of about 200 to about 7100 kPa.

Oxidation involves the oxidation of hydrocarbons to oxygen-containing compounds, such as aldehydes. The hydrocarbons include alkanes, alkenes, typically with carbon numbers from 2 to 15, and alkyl aromatics; linear, branched, and cyclic alkanes and alkenes can be used. Oxygenates that are not fully oxidized to ketones or carboxylic acids can also be subjected to oxidation processes, as well as sulfur compounds that contain —S—H moieties, thiophene rings, and sulfone groups. The process is carried out by placing an oxidation catalyst in a reaction zone and contacting the feed stream which contains the desired hydrocarbons with the catalyst in the presence of oxygen. The type of reactor which can be used is any type well known in the art such as fixed-bed, moving-bed, multi-tube, CSTR, fluidized bed, etc. The feed stream can be flowed over the catalyst bed either up-flow or down-flow in the liquid, vapor, or mixed phase. In the case of a fluidized-bed, the feed stream can be flowed co-current or counter-current. In a CSTR, the feed stream can be continuously added or added batch-wise. The feed stream contains the desired oxidizable species along with oxygen. Oxygen can be introduced either as pure oxygen or as air, or as liquid phase oxidants including hydrogen peroxide, organic peroxides, or peroxy-acids. The molar ratio of oxygen ($O_2$) to alkane can range from about 5:1 to about 1:10. In addition to oxygen and alkane or alkene, the feed stream can also contain a diluent gas selected form nitrogen, neon, argon, helium, carbon dioxide, steam or mixtures thereof. As stated, the oxygen can be added as air which could also provide a diluent. The molar ratio of diluent gas to oxygen ranges from greater than zero to about 10:1. The catalyst and feed stream are reacted at oxidation conditions which include a temperature of about 300° C. to about 600° C., a pressure of about 101 kPa to about 5,066 kPa and a space velocity of about 100 to about 100,000 $hr^{-1}$.

Hydrogenation involves the addition of hydrogen to hydrogenatable hydrocarbon compounds. Alternatively hydrogen can be provided in a hydrogen-containing compound with ready available hydrogen, such as tetralin, alcohols, hydrogenated naphthalenes, and others via a transfer hydrogenation process with or without a catalyst. The hydrogenatable hydrocarbon compounds are introduced into a hydrogenation zone and contacted with a hydrogen-rich gaseous phase and a hydrogenation catalyst in order to hydrogenate at least a portion of the hydrogenatable hydrocarbon compounds. The catalytic hydrogenation zone may contain a fixed, ebulated or fluidized catalyst bed. This reaction zone is typically at a pressure from about 689 kPa gauge (100 psig) to about 13790 kPa gauge (2000 psig) with a maximum catalyst bed temperature in the range of about 177° C. (350° F.) to about 454° C. (850° F.). The liquid hourly space velocity is typically in the range from about 0.2 $hr^{-1}$ to about 10 $hr^{-1}$ and hydrogen circulation rates from about 200 standard cubic feet per barrel (SCFB) (35.6 $m^3/m^3$) to about 10,000 SCFB (1778 $m^3/m^3$).

Figure 2:
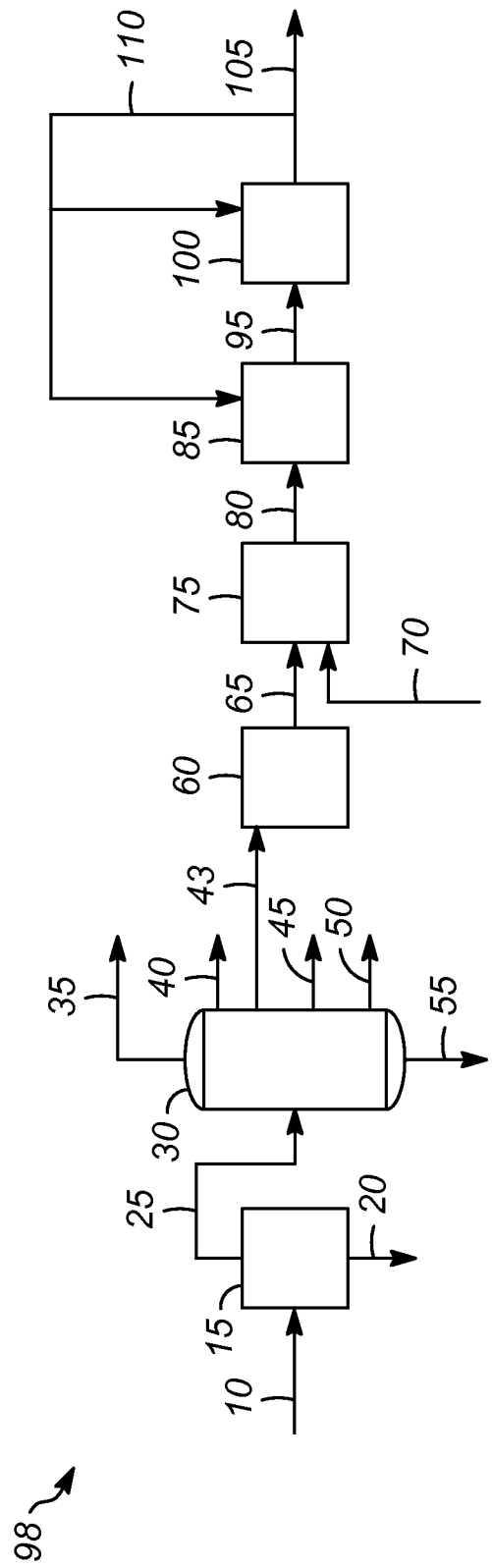
FIG. 2 is an illustration of a second embodiment process of the present invention.

FIG. 2 shows a second embodiment process 98. FIG. 2 depicts a process similar to that of FIG. 1, except that the effluent stream 95 from the dehydrogenation zone 85 is fed to an additional transalkylation zone 100, in which the effluent stream is transalkylated to produce a xylene stream 105. The additional transalkylation zone 100 normally operates at conditions including a temperature in the range of about 130° C. to about 540° C., and a pressure ranging from about 1.4 MPa (200 psig) to about 4.1 MPa (600 psig). The transalkylation reaction can be effected over a wide range of space velocities. That is, volume of charge per volume of catalyst per hour; weight hourly space velocity (WHSV) generally is in the range of from about 0.1 to about 30 $hr^{-1}$. The catalyst is typically selected to have relatively high stability at a high activity level. At least a portion 110 of effluent 105 from the additional transalkylation zone 100 including one or more of A9+ aromatics, benzene, and toluene can be recycled from the additional transalkylation zone to the dehydrogenation zone 85 or transalkylation zone 100. This recycle will be conducted after removal of at least some of the target product (normally xylenes and in some cases benzene) to promote continued transalkylation to these desired species. Conversion to the desired species is limited by equilibrium so removal of the desired product species and recycle of the rest promotes further conversion of toluene and A9's and greater to benzene and xylenes.

Figure 3:
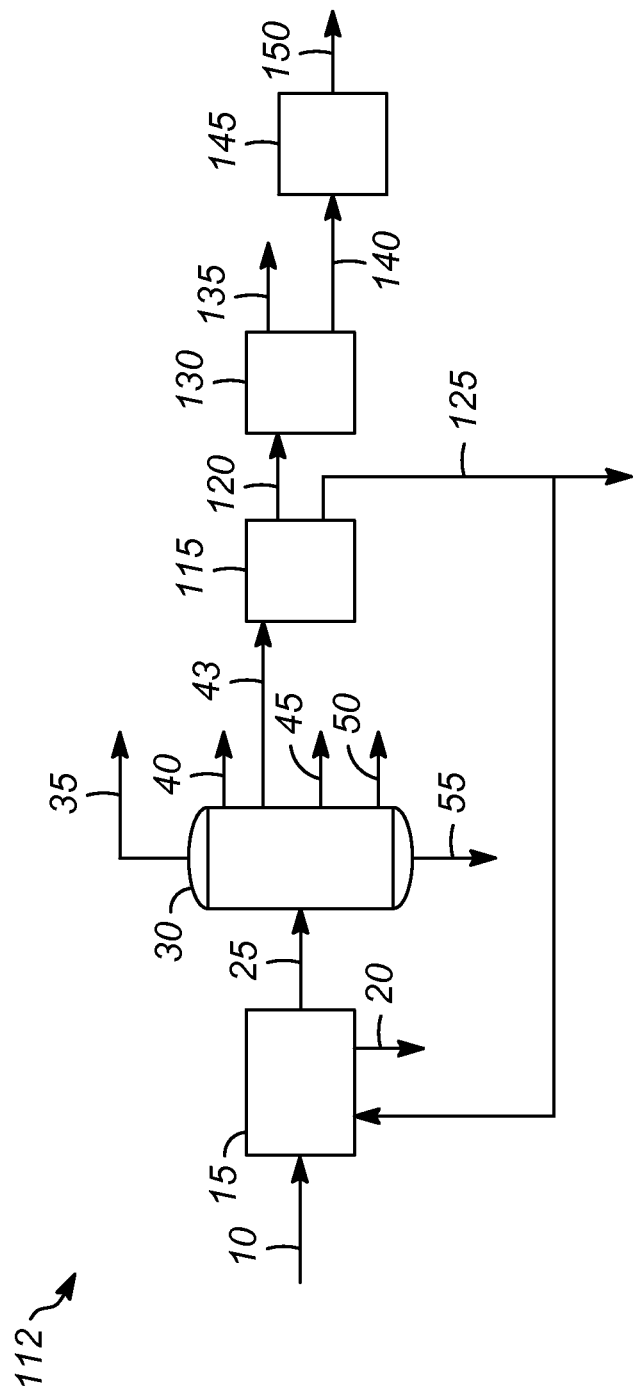
FIG. 3 is an illustration of a third embodiment process of the present invention.

FIG. 3 shows a third embodiment process 112, in which like reference characters represent similar processes, feeds, or products. In FIG. 3, at least one hydrocarbon stream, such as the light oil fraction 40, the middle oil fraction 43 or the heavy oil fraction 45 having polycyclic aromatics (the middle oil fraction 43 is shown in FIG. 3), is introduced to a hydrocracking zone 115. Example polycyclic aromatics include naphthalene, alkyl naphthalenes, tetralin, benzothiophene, oxygenated polyaromatics, fluorene, anthracene, phenanthrene, and others.

The hydrocracking conditions in the hydrocracking zone 115 include a temperature of about 290° C. (550° F.) to about 468° C. (875° F.), and a liquid hourly space velocity (LHSV) of about 1.0 to less than about 2.5 $hr^{-1}$, and a hydrogen rate of about 421 to about 2,527 $Nm^3/m^3$ oil (2,500-15,000 scf/bbl). Typical hydrocracking catalysts include amorphous silica-alumina bases or low-level zeolite bases combined with one or more Group VIII or Group VIB metal hydrogenating components, or a crystalline zeolite cracking base upon which is deposited a Group VIII metal hydrogenating component. Additional hydrogenating components may be selected from Group VIB for incorporation with the zeolite base.

In the hydrocracking zone 115, a first portion of the polycyclic aromatics in the hydrocarbon stream, e.g., a portion of streams 43 or 45, is converted to monocyclic aromatics. A second portion of the polycyclic aromatics is hydrogenated in the hydrocracking zone 115 to form a hydrogen donor molecule stream 125. Such hydrogen donor molecules are typically, but not exclusively, aliphatic compounds such as multi-ring naphtheno-aromatics like tetralin or single or multi-ring naphthenes or paraffins. The hydrogen donor molecule stream can be recycled 125 to the upstream pyrolysis zone 15, to an upstream hydrotreating zone (not shown), or used in other processes.

A light fraction output (C5−) 120 from the hydrocracking zone 115 can be output to a hydrogen production zone 130, such as a steam cracking zone. Example steam cracking conditions include a coil outlet temperatures of about 650° C. to about 900° C. and residence times from 0.5 to 5 seconds, whereby the hydrocarbon stream is diluted with steam. In the hydrogen production zone, an olefin stream 135 is produced as well as a hydrogen stream 140. The hydrogen stream 140 can be introduced to another zone for processing, such as a hydroprocessing zone 145 to produce one or more products 150. Example hydroprocessing conditions are described above. The hydrogen production zone 130 can also be a steam reforming zone. In a steam reforming zone, a hydrocarbon mixture is reacted over a steam reforming catalyst, e.g., containing nickel, at temperatures between about 600° C. and about 950° C., and preferably at temperatures exceeding about 800° C. Pressures are commensurate with downstream processes, and most typically are between about 1 MPa (about 10 bars) and about 5 MPa (about 50 bars). The effluent of the steam reforming zone includes $H_2$, CO, $CO_2$, and methane.

The third embodiment process may also be used to process hydrocarbon streams other than the hydrocarbon streams 40, 43, 45, 50 produced by fractionating coal tar. Thus, the process 112 is not intended to be limited to processing a coal tar feed. Other suitable hydrocarbon streams that can be used to provide hydrogen donor molecules include vacuum gas oil (VGO), light cycle oil (LCO), coker gas oil, and others. In such processes, the hydrogen donor molecule stream 125 from the hydrocracking zone 115 can be used in various processes, including hydroprocessing, fluid catalyzed cracking, steam naphtha cracking, etc.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A process comprising:
   pyrolyzing coal to produce a coal tar stream;
   fractionating said coal tar stream to provide at least one hydrocarbon stream comprising polycyclic aromatics;
   hydrotreating the hydrocarbon stream in a hydrotreating zone in the presence of a catalyst containing at least one group VIII metal and at least one group VI metal to remove sulfur, nitrogen, and metals and to saturate hydrocarbon with double or triple bonds to produce a hydrotreated stream;
   hydrocracking the hydrotreated stream in the presence of catalyst comprising amorphous silica-alumina bases or low-level zeolite bases combined with one or more group VIII or group VIB metal hydrogenating metal in a hydrocracking zone to crack a first portion of the polycyclic aromatics to mono-aromatics and saturate mono-aromatics to cycloparaffin; and hydrogenating a second portion of the polycyclic aromatics in the hydrocracking zone to form a hydrogen donor molecules including tetralin, naphthene, and paraffins;
   introducing a light fraction (C5−) output from the hydrocracking zone to an olefin production zone;
   producing olefins in the light fraction output by steam cracking, wherein excess hydrogen is produced;
   introducing the excess hydrogen to a hydroprocessing zone; and
   recycling a first portion of hydrogen donor molecule stream to one of the pyrolyzing steps and/or the hydrotreating step.

2. The process of claim 1 further comprising introducing the hydrogen donor molecule to an upstream pyrolysis zone.

3. The process of claim 1 further comprising introducing the hydrogen donor molecule to an upstream hydrotreating zone.

4. The process of claim 1 wherein the portion of the polycyclic aromatics comprises tetralin.

5. The process of claim 1 further comprising pyrolyzing a coal feed in a pyrolysis zone to provide at least a coke stream and the coal tar feed.

6. The process of claim 5, further comprising introducing the hydrogen donor molecule to the pyrolysis zone.

* * * * *